(12) United States Patent
Lednev (10) Patent No.: US 9,891,108 B2
(45) Date of Patent: Feb. 13, 2018

(54) SPECTROSCOPIC METHOD FOR ALZHEIMER'S DISEASE DIAGNOSIS

(71) Applicant: THE RESEARCH FOUNDATION FOR THE STATE UNIVERSITY OF NEW YORK, Albany, NY (US)

(72) Inventor: Igor K. Lednev, Glenmont, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 14/432,873

(22) PCT Filed: Oct. 2, 2013

(86) PCT No.: PCT/US2013/063118
§ 371 (c)(1),
(2) Date: Apr. 1, 2015

(87) PCT Pub. No.: WO2014/055683
PCT Pub. Date: Apr. 10, 2014

(65) Prior Publication Data
US 2015/0276482 A1    Oct. 1, 2015

Related U.S. Application Data

(60) Provisional application No. 61/744,743, filed on Oct. 3, 2012.

(51) Int. Cl.
*G01J 3/44*   (2006.01)
*G01N 21/65*  (2006.01)
(Continued)

(52) U.S. Cl.
CPC ............... *G01J 3/44* (2013.01); *G01N 21/65* (2013.01); *G01N 21/658* (2013.01); *G01N 33/49* (2013.01);
(Continued)

(58) Field of Classification Search
None
See application file for complete search history.

(56) References Cited

U.S. PATENT DOCUMENTS 6,738,651 B1    5/2004  Jackson
7,595,873 B1 *  9/2009  Deck ........................ G01J 3/02
                                                          356/301
(Continued)

FOREIGN PATENT DOCUMENTS

EP    2700933 A1   2/2014
ES    2222779 A1   2/2005
(Continued)

OTHER PUBLICATIONS

Georganopoulou, Dimitra G., et al. "Nanoparticle-based detection in cerebral spinal fluid of a soluble pathogenic biomarker for Alzheimer's disease." Proceedings of the National Academy of Sciences of the United States of America 102.7 (2005): 2273-2276.*
(Continued)

*Primary Examiner* — Kara E Geisel
*Assistant Examiner* — Shawn DeCenzo
(74) *Attorney, Agent, or Firm* — LeClairRyan, a Professional Corporation (57) ABSTRACT

The present invention relates to a method for detecting Alzheimer's disease in a subject. This method involves providing a sample from the subject, subjecting the sample to a spectroscopic analysis to produce a spectroscopic signature for the sample, determining whether the spectroscopic signature for the sample corresponds to an Alzheimer's disease spectroscopic signature, and identifying a subject as having Alzheimer's disease where the spectroscopic signature for the sample from that subject corresponds to the spectroscopic signature for Alzheimer's disease. Also disclosed is a method for monitoring Alzheimer's disease progression in a subject, involving providing a
(Continued)

sample from a subject with Alzheimer's disease, subjecting the sample to a spectroscopic analysis to produce a spectroscopic signature for the sample, comparing the spectroscopic signature for the sample to a prior spectroscopic signature from the subject or to a spectroscopic signature standard for a specific stage of Alzheimer's disease, and determining the progression of Alzheimer's disease in the subject based on said comparing.

18 Claims, 6 Drawing Sheets

(51) Int. Cl.
*G01N 33/68* (2006.01)
*G01N 33/49* (2006.01)

(52) U.S. Cl.
CPC . *G01N 33/6896* (2013.01); *G01N 2800/2821* (2013.01)

(56) References Cited

U.S. PATENT DOCUMENTS

| | | | |
|---|---|---|---|
| 2008/0070995 | A1 | 3/2008 | Westbrook et al. |
| 2010/0070197 | A1* | 3/2010 | Wang .................. G01J 3/02 702/22 |
| 2010/0105098 | A1* | 4/2010 | Frederiske ........... A61B 5/0059 435/29 |
| 2010/0264332 | A1* | 10/2010 | Coker .................... G01N 21/64 250/459.1 |
| 2011/0143961 | A1* | 6/2011 | Lednev ................. G01N 21/65 506/13 |
| 2012/0316446 | A1* | 12/2012 | Vukelic ................. G01N 21/65 600/476 |
| 2014/0312231 | A1 | 10/2014 | Hernandez et al. |

FOREIGN PATENT DOCUMENTS

| | | |
|---|---|---|
| ES | 2246113 A1 | 2/2006 |
| ES | 2396106 A1 | 2/2013 |
| WO | 2004/010122 A1 | 1/2004 |
| WO | 2005/043136 A1 | 5/2005 |
| WO | 2009/005186 A1 | 1/2009 |
| WO | 2013/021087 A1 | 2/2013 |
| WO | 2014/029767 A1 | 2/2014 |

OTHER PUBLICATIONS

Chen, P., et al. "Laser Raman detection of platelet as a non-invasive approach for early and differential diagnosis of Alzheimer's disease." Laser Physics Letters 8.7 (2011): 547.*

PCT International Search Report and Written Opinion for corresponding International Application PCT/US2013/063118 (dated Jan. 16, 2014).

Carmona et al., "Discrimination Analysis of Blood Plasma Associated with Alzheimer's Disease Using Vibrational Spectroscopy," J. Alzheimer's Disease 34(4):911-920 (2013).

"Novel Spectroscopic Method for Alzheimer's Disease Diagnosis," http://www.nycapresearchalliance.org/novel-spectroscopic-method-alzheimer%E2%80%99s-disease-diagnosis (Oct. 3, 2012).

International Preliminary Report on Patentability for corresponding International Application PCT/US2013/063118 (dated Apr. 7, 2015).

* cited by examiner

SPECTROSCOPIC METHOD FOR ALZHEIMER'S DISEASE DIAGNOSIS

This application claims the priority benefit of U.S. Provisional Patent Application Ser. No. 61/744,743, filed Oct. 3, 2012, which is hereby incorporated by reference in its entirety.

FIELD OF THE INVENTION

The present invention relates to a spectroscopic method for Alzheimer's disease diagnosis.

BACKGROUND OF THE INVENTION

Alzheimer's disease (AD) is the most widespread type of dementia in elderly population of the world. It is also among the most serious health problems in the industrialized nations including United States. This neurodegenerative disease is progressive, incurable and lethal. More than 5.1 million Americans suffer from AD and 100 million people worldwide, and this number is expected to increase dramatically by the year of 2050 (Brookmeyer et al., *Alzheimer's & dementia: the Journal of the Alzheimer's Assoc.* 7:61-73 (2011); Sperling et al., *Alzheimer's and Dementia* 7:280-292 (2011)).

AD is characterized by a broad number of clinical manifestations, such as a gradual loss of short-term memory, language problems, progressive difficulty performing familiar tasks, disorientation to time and place, impairments in abstract thinking, disturbances in behavior and personality, sleep disturbances, depression, anxiety, psychosis and dementia (Farlow, *American Journal of Health-System Pharmacy:AJHP:Official Journal of the American Society of Health-System Pharmacists* 55(Suppl 2):S5-10 (1998); Monien et al., *Expert Review of Neurotherapeutics* 6:1293-1306 (2006)). These symptoms result from significant morphological alterations of the brain tissue caused by processes related to formation of Amyloid beta (Aβ) plaques and neurofibrillary tangles (NFTs).

The destructive pathophysiological process is thought to last many years with nearly no specific symptoms before the clinical diagnosis of AD can be made. Since the deferential diagnosis for dementias heavily relies on clinical criteria it is often a complex and difficult process. Slow initiation of AD during the "preclinical" phase could provide a critical opportunity for therapeutic intervention. The treatment at the early stages of disease progression would be the most effective allowing interference with the pathological process before irreversible damage occurs and keeping patients in an independent functional state for as long as possible. Therefore, early diagnosis of AD in patients at risk is of great importance.

Intensive investigation by many research teams has been made to identify blood based biomarkers that can be used for clinical laboratory tests, including metabolomics and proteomic analyses (Banks et al., *The Lancet* 356:1749-1756 (2000); Sudworth et al., *European Conference on Biomedical Optics* (2005); Burns et al., *J. Alzheimers Dis.* 17:391-397 (2009); Zellner et al., *Acta Neuropathol.* 118:181-195 (2009); Blennow et al., *Nature Reviews Neurology*, 6:131-144 (2010)). Although applied methods are expensive with regard to time, labor and financial resources and thus difficult to translate into the clinical laboratory, the results of this study showed that such biomarkers exist and provided very promising opportunities in the field of AD diagnosis. Several chemical analytes showed the potential to be AD biomarkers, including oxidative stress biomarkers, metabolite profile and protein-expression profile (Burns et al., *J. Alzheimers Dis.* 17:391-397 (2009); Teunissen et al., *Neurobiol. Aging* 24:893-902 (2003); Irizarry, *NeuroRx: The Journal of the American Society for Experimental NeuroTherapeutics* 1:226-234 (2004); Britschgi et al., *Arch. Neurol.* 66:161-165 (2009); Kork et al., *Current Alzheimer Research* 6:519-524 (2009)). However, none of them was accepted as a specific diagnostic biomarker applicable for a routine diagnostic test of AD when evaluated separately.

The development of a universal test to detect the presence of an AD biomarker signature in blood would have tremendous utility. With respect to the complexity of pathophysiological processes during AD progression, the diagnostic strategy can benefit greatly from simultaneous detection of various serum or plasma biomarkers.

Recently, Raman spectroscopy has been proved to be very suitable to study biochemical signatures of a number of diseases. It has been applied to diagnose different types of cancer, diabetes, atherosclerosis, and Parkinson's disease (Koo et al., *Diabetes Technol. Ther.* 1:153-157 (1999); Pichardo-Molina et al., *Lasers Med. Sci.* 22:229-236 (2007); Schipper et al., *Biomark. Med.* 2:229-238 (2008)). Raman spectroscopy provides specific information on structure, conformation and composition of macromolecules such as nucleic acids, proteins and lipids. This information is unique for each molecule. Therefore, Raman spectroscopy can provide fingerprinting type of information for the current biochemical state of blood. A diagnostic blood test can then be made based on a comparison of the obtained spectroscopic changes in blood of patient under evaluation with a developed library of Raman spectroscopic signatures for AD.

Raman spectroscopy provides unique information on the overall biochemical composition of a biological sample including the variations in the structure and conformation of contributing biomolecules. Raman scattering of human serum arise from various biomacromolecules, such as proteins, nucleic acids and lipids. Typically, the Raman signal is relatively weak. Colloidal silver nanoparticles as a SERS-active substrate are typically used to enhance the Raman scattering.

The present invention is intended to overcome these and other deficiencies in the art.

SUMMARY OF THE INVENTION

The present invention relates to a method for detecting Alzheimer's disease in a subject. This method involves providing a sample from the subject, subjecting the sample to a spectroscopic analysis to produce a spectroscopic signature for the sample, determining whether the spectroscopic signature for the sample corresponds to an Alzheimer's disease spectroscopic signature, and identifying a subject as having Alzheimer's disease where the spectroscopic signature for the sample from that subject corresponds to the spectroscopic signature for Alzheimer's disease.

Another aspect of the present invention relates to a method for monitoring Alzheimer's disease progression in a subject. This method involves providing a sample from a subject with Alzheimer's disease, subjecting the sample to a spectroscopic analysis to produce a spectroscopic signature for the sample, comparing the spectroscopic signature for the sample to a prior spectroscopic signature from the subject or to a spectroscopic signature standard for a specific stage of Alzheimer's disease, and determining the progression of Alzheimer's disease in the subject based on said comparing.

A Raman spectroscopic blood-based test will be useful in complementing clinical assessment for effective and accurate AD diagnosis. The method described in the present invention will allow for more labor, time, and cost effective Alzheimer's disease detection and will be useful for screening elderly patient populations for Alzheimer's disease progression.

BRIEF DESCRIPTION OF THE DRAWINGS

FIGS. 1A-D show Raman spectra of human blood serum samples. FIG. 1B shows mean spectra of healthy controls (red line), mild (green line) and moderate (blue line) AD subjects. FIG. 1C shows differential spectra: moderate AD—healthy controls (red line), mild AD—healthy controls (green line), AD—healthy controls (blue line). FIG. 1D shows differential spectra (FIG. 1C) within the Informative spectroscopic region (900 and 1750 cm−1).

FIGS. 2A-B show SVMDA classification of Raman spectra of human blood serum samples.

FIG. 3A-B show SVMDA classification of Raman spectra of human blood serum samples.

FIGS. 6A-B show that SVM Discriminant analysis of SERS spectra of serum allows for the differentiation between AD patients and healthy individuals. Red triangles and blue squares correspond to single spectra acquired from AD and control samples, respectively.

FIG. 7A-B show that SVM Discriminant analysis of SERS spectra of serum allows for the differentiation between AD patients and individuals with other types of dementia. Red triangles and green squares correspond to single spectra acquired from AD and other types of dementia samples, respectively.

FIGS. 8A-B show the standard deviations for each class of SERS spectra of serum samples. Standard deviation for AD class of spectra (blue line) and control samples (green line). The difference spectrum is shown as a red line.

DETAILED DESCRIPTION OF THE INVENTION

One aspect of the present invention relates to a method for detecting Alzheimer's disease in a subject. This method involves providing a sample from the subject, subjecting the sample to a spectroscopic analysis to produce a spectroscopic signature for the sample, determining whether the spectroscopic signature for the sample corresponds to an Alzheimer's disease spectroscopic signature, and identifying a subject as having Alzheimer's disease where the spectroscopic signature for the sample from that subject corresponds to the spectroscopic signature for Alzheimer's disease.

In the present invention, the term "spectroscopic signature" refers to a single spectrum, an averaged spectrum, multiple spectra, or any other spectroscopic representation of the sample.

In one embodiment, the sample is human serum. Alternatively, the sample can be (whole) blood, plasma, or cerebral spinal fluid.

In one embodiment, the method further includes determining the stage of Alzheimer's disease in the subject based on the spectroscopic signature for the sample from the subject. The method determines the stage of Alzheimer's disease as being mild or moderate.

In accordance with the present invention, the determining step includes comparing the spectroscopic signature for the sample from the subject to a reference spectroscopic signature and determining the presence of Alzheimer's disease in the subject based on the comparing.

In yet another embodiment the method further includes determining whether the subject has a neurodegenerative disease other than Alzheimer's disease based on the spectroscopic signature for the sample from the subject. These other neurodegenerative diseases include: Parkinson's disease, Huntington disease, Amyotrophic lateral sclerosis (ALS), multiple sclerosis (MS), and stroke.

The spectroscopic analysis can involve Raman spectroscopy, vibrational spectroscopy, and combinations thereof. The Raman spectroscopy can be NIR Raman spectroscopy or Surface Enhanced Raman spectroscopy (SERS).

Raman spectroscopy is a spectroscopic technique which relies on inelastic or Raman scattering of monochromatic light to study vibrational, rotational, and other low-frequency modes in a system (Gardiner, D. J., *Practical Raman Spectroscopy*, Berlin: Springer-Verlag, pp. 1-3 (1989), which is hereby incorporated by reference in its entirety). Vibrational modes are very important and very specific for certain types of chemical bonds in molecules. They provide a fingerprint by which a molecule can be identified. The Raman effect is obtained when a photon interacts with the electron cloud of a molecular bond, exciting the electrons into a virtual state. The scattered photon is shifted to lower frequencies (Stokes process) or higher frequencies (anti-Stokes process) as it releases energy to or from the molecule, respectively. The polarizability change in the molecule will determine the Raman scattering energy, while the Raman shift will be equal to the vibrational intensity involved.

Fluorescence interference is the largest problem with Raman spectroscopy and is perhaps the reason why the latter technique has not been more popular in the past. If a sample contains molecules that fluoresce, the broad and much more intense fluorescence peak will mask the sharp Raman peaks of the sample. There are a few remedies to this problem. One solution is to use deep ultraviolet (DUV) light for exciting Raman scattering (Lednev I. K., "Vibrational Spectroscopy: Biological Applications of Ultraviolet Raman Spectroscopy," in: V. N. Uversky, and E. A. Permyakov, *Protein Structures, Methods in Protein Structures and Stability Analysis* (2007), which is hereby incorporated by reference in its entirety). Practically no condensed face exhibits fluorescence below ~250 nm. Possible photodegradation of biological samples is an expected disadvantage of DUV Raman spectroscopy. Another option to eliminate fluorescence interference is to use a near-IR (NIR) excitation for Raman spectroscopic measurement. Finally, surface enhanced Raman spectroscopy (SERS) which involves a rough metal surface can also alleviate the problem of fluorescence (Thomas et al., "Raman Spectroscopy and the Forensic Analysis of Black/Grey and Blue Cotton Fibers Part 1: Investigation of the Effects of Varying Laser Wavelength," *Forensic Sci. Int.* 152:189-197 (2005), which is hereby incorporated by reference in its entirety). However, this method requires direct contact with the analyte and cannot be considered to be nondestructive.

Basic components of a Raman spectrometer are (i) an excitation source; (ii) optics for sample illumination; (iii) a single, double, or triple monochromator; and (iv) a signal processing system consisting of a detector, an amplifier, and an output device.

Typically, a sample is exposed to a monochromatic source usually a laser in the visible, near infrared, or near ultraviolet range. The scattered light is collected using a lens and is focused at the entrance slit of a monochromator. The monochromator, which is set for a desirable spectral resolution rejects the stray light in addition to dispersing incoming radiation. The light leaving the exit slit of the monochromator is collected and focused on a detector (such as a photodiode arrays (PDA), a photomultiplier (PMT), or charge-coupled device (CCD)). This optical signal is converted to an electrical signal within the detector. The incident signal is stored in computer memory for each predetermined frequency interval. A plot of the signal intensity as a function of its frequency difference (usually in units of wavenumbers, $cm^{-1}$) will constitute the Raman spectroscopic signature.

Raman signatures are sharp and narrow peaks observed on a Raman spectrum. These peaks are located on both sides of the excitation laser line (Stoke and anti-Stoke lines). Generally, only the Stokes region is used for comparison (the anti-Stoke region is identical in pattern, but much less intense) with a Raman spectrum of a known sample. A visual comparison of these set of peaks (spectroscopic signatures) between experimental and known samples is needed to verify the reproducibility of the data. Therefore, establishing correlations between experimental and known data is required to assign the peaks in the molecules and identify a specific component in the sample.

The types of Raman spectroscopy suitable for use in conjunction with the present invention include, but are not limited to, conventional Raman spectroscopy, Raman microspectroscopy, near-field Raman spectroscopy, including but not limited to the tip-enhanced Raman spectroscopy, surface enhanced Raman spectroscopy (SERS), surface enhanced resonance Raman spectroscopy (SERRS), and coherent anti-Stokes Raman spectroscopy (CARS). Also, both Stokes and anti-Stokes Raman spectroscopy could be used.

The vibrational spectroscopy can involve Infrared (IR) absorption, Fourier Transform Infrared absorption (FTIR), or Attenuated Total Reflection (ATR) FTIR.

Fourier transform infrared (FTIR) spectroscopy is a versatile tool for the detection, estimation and structural determination of organic compounds and for determination of the chemical structure of many inorganic compounds. In infrared spectroscopy (IR), IR radiation is passed through a sample. Some of the infrared radiation is absorbed by the sample and some is transmitted. The resulting spectrum represents a fingerprint of a sample with absorption peaks which correspond to the frequencies of vibration between the bonds of the atoms making up the material.

Basic components of FTIR are (i) a source; (ii) an interferometer; (iii) a sample; (iv) a detector; (v) computer.

Infrared energy is emitted from a glowing black-body source. This beam passes through an aperture which controls the amount of energy presented to the sample (and, ultimately, to the detector). The beam enters the interferometer where "spectral encoding" takes place. The resulting interferogram signal then exits the interferometer. The beam enters the sample compartment where it is transmitted through or reflected off of the surface of the sample; depending on the type of analysis being accomplished, this is where specific frequencies of energy, which are uniquely characteristic of the sample, are absorbed. The beam finally passes to the detector for final measurement. The measured signal is digitized and sent to the computer where the Fourier transformation takes place.

Microscopic-attenuated total reflectance (ATR) Fourier transform infrared (FT-IR) analysis is nondestructive, with analysis times competitive to current methodologies, and offers a molecular "fingerprint" of the analyzed sample. The vibrational signatures collected from the sample are easily discernible by the naked eye. Furthermore, this vibrational "fingerprint" targets a wider range of chemicals as compared to current methodologies, increasing the selectivity of the method. The optics of ATR-FT-IR imaging provides pseudo-immersion analysis. The high refractive index of the germanium ATR crystal increases the numerical aperture of the optics, enhancing spatial resolution by a factor of 4, without the use of a synchrotron light source (ATR accessories An overview, *PerkinElmer Life and Analytical Sciences*, (2004), which is hereby incorporated by reference in its entirety). Exhaustive research applying micro-ATR-FT-IR chemical imaging (mapping) to the fields of bio-medical (Chan et al., *Appl. Spectrosc.* 59:149 (2005); Anastassopoulou et al., *Vibrational Spectroscopy*, 51:270 (2009); Kazarian et al., *Biochimica et Biophysica Acta* (BBA)—*Biomembranes*, 1758:858 (2006); Kazarian et al., *Analyst*, 138:1940 (2013), which are hereby incorporated by reference in their entirety) and forensic research (Dirwono et al., *Forensic Science International*, 199:6 (2010); Ng et al., *Anal. and Bioanal. Chem.* 394:2039 (2009); Spring et al., *Anal. and Bioanal. Chem.*, 392:37 (2008), which are hereby incorporated by reference in their entirety) have been reported.

Another aspect of the present invention relates to a method for monitoring Alzheimer's disease progression in a subject. This method involves providing a sample from a subject with Alzheimer's disease, subjecting the sample to a spectroscopic analysis to produce a spectroscopic signature for the sample, comparing the spectroscopic signature for the sample to a prior spectroscopic signature from the subject or to a spectroscopic signature standard for a specific stage of Alzheimer's disease, and determining the progression of Alzheimer's disease in the subject based on said comparing.

This aspect of the present invention is carried out using the same types of samples and techniques as described above.

EXAMPLE

The following Example is intended to illustrate the practice of the present invention, but it is in no way intended to limit the scope of the claimed invention.

Example 1—Clinical Subjects and Protocols

Studied subjects were recruited at Alzheimer's center at Albany Medical College (AMC). All subjects have undergone a review of their medical history and clinical assessments to determine their level of dementia in accordance with currently accepted AD diagnosis standards. Their clinical diagnoses were established by a trained neurologist. The control group consisted of age- and sex-matched control subjects free of any neurological and psychiatric ailments, who signed a consent form for the study. The research protocol for human studies was reviewed and approved by the University at Albany Institutional Review Board (IRB), the Albany Medical College IRB. The authorized study personal obtained a written informed consent from potential study subjects prior to their participation. A summary of demographic information for study subjects is presented in Table 1.

The group of AD patients consists of 20 clinically diagnosed subjects. Their cognitive functions were evaluated using Clinical Dementia Rating (CDR).

The group of Healthy Controls (HC) consisted of 10 subjects (Table 1). Control volunteers were mainly patients' spouses and, therefore, had relatively similar ethnic background, socioeconomic and environmental factors, such as age, education, race, religion, social and economic status, diet, and everyday lifestyle.

TABLE 1

Summary of Demographic Information on the Research Subjects.

|  | AD (n = 20) | HC (n = 10) |
|---|---|---|
| Age in years ± SD | 74 ± 9.3 | 68 ± 11 |
| Male (%) | 50 | 50 |
| Female (%) | 50 | 50 |
| AD duration in years ± SD |  |  |
| Moderate stage | 10 | N\A |
| Mild stage | 10 | N\A |
| Medications |  |  |
| Donepezil | 6 |  |
| Namenda | 6 |  |
| Sertraline | 5 |  |
| Rivastigmine | 2 |  |
| Risperedone | 1 |  |
| Citalopram | 1 |  |
| Galantamine | 2 |  |

Example 2—Sample Preparation

After overnight fasting, a peripheral blood sample of 5 mL was collected and immediately processed into aliquots of anti-coagulated whole blood, plasma, and serum and stored at −80° C. until used for the present analysis. EDTA was used as an anticoagulant. The blood samples from each subject were drawn and handled identically.

Prior to Raman measurements, a blood serum sample was defrosted on ice and a 40-µL drop of blood serum sample was placed on a microscopic glass slide covered with aluminum foil and allowed to dry completely under gentle air flow within 5 min. The aluminum foil was used as a substrate which produces a low fluorescence signal.

Example 3—Raman Spectroscopic Measurements

The Raman spectra were collected with a RenishawinVia confocal Raman spectrometer equipped with a research-grade Leica microscope, 50× long-range objective (numerical aperture of 0.35). All measurements were performed via automatic mapping using the lower plate of a Renishaw PRIOR automatic stage system. The spectra were recorded with WiRE 3.2 software in the range of 400-1800 $cm^{-1}$ under a 785 nm excitation wavelength of diode laser. To avoid photodegradation of the sample, the laser power was reduced to 11.5 mW (50% of the maximum laser power). An automatic stage system allowed a pre-program mapping procedure and scanning of the sample within the area of 2000×2000 µm to be carried out. The sequential spectra from 120 adjacent spots of a sample were measured with two 10 second accumulations at each point. This procedure ensures a thorough representation of the sample and accounts for its possible heterogeneity.

The Raman spectra of human blood serum from 20 AD and 10 Healthy Controls subjects were recorded and analyzed. Spectroscopic data from each group are presented and analyzed in further detail below.

Example 4—AD Subjects and Healthy Controls

Figure 1A:
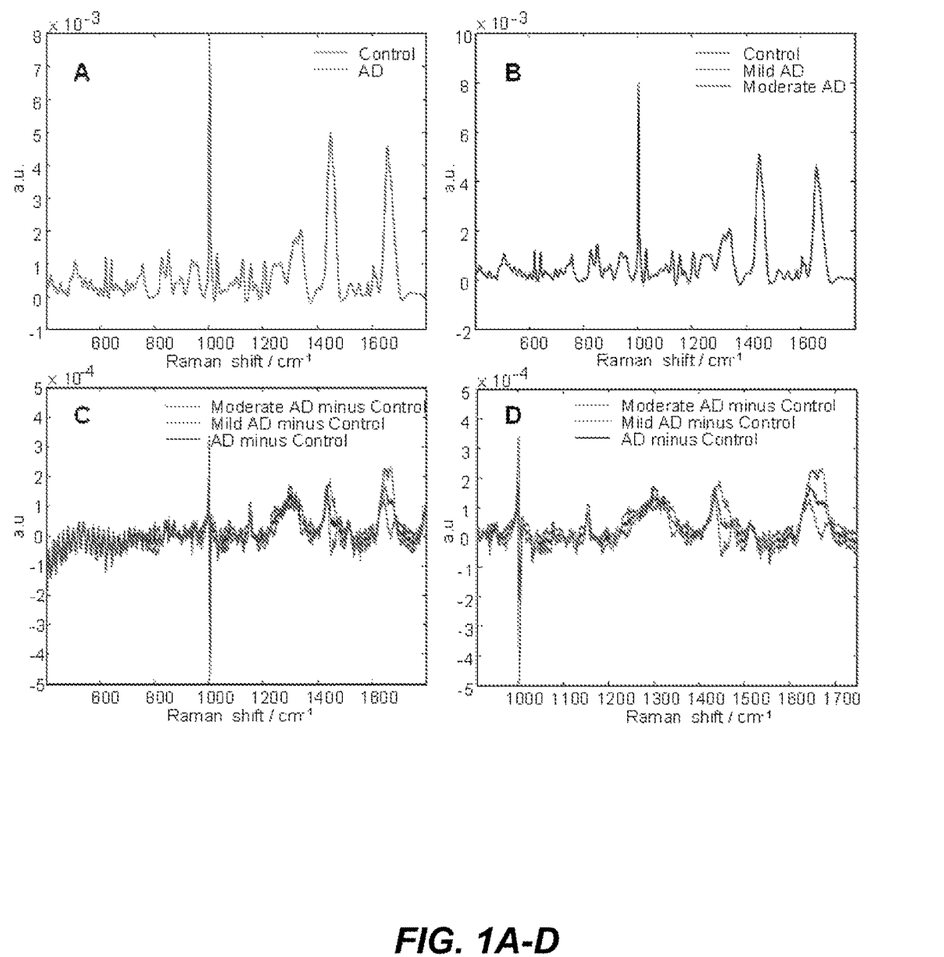
FIG. 1A shows mean spectra of healthy controls (red line) and AD (combined mild and moderate groups, green line) subjects.

The sample cohort consisted of 10 healthy controls and 20 AD subjects. Among AD cluster, ten subjects were assigned to a moderate AD group, while other ten subjects to a mild AD group (see Example 1). FIG. 1A and FIG. 1B show mean spectra of healthy controls and AD (moderate and mild AD) groups, respectively. The mean spectra are very similar and do not provide apparent spectroscopic differences between groups under consideration. Correspondent difference spectra (FIG. 1C) are more informative and have characteristic features within 900-1750 cm$^{-1}$ spectral region. Difference spectrum below 900 cm$^{-1}$ is a typical sinusoid-like instrumental function frequently observed at low wavenumbers. Only the informative region between 900 and 1750 cm$^{-1}$ was used for the following analysis (FIG. 1D).

The initial data set was reduced by eliminating Raman spectra with high variance of additive Gaussian noise. The threshold was set to cut off 15% of the noisiest experimental Raman spectra. An analysis was performed using the remaining 85% of Raman data divided in three classes: healthy controls, moderate AD, and mild AD. Raman spectra recorded with ~1 cm$^{-1}$ spectral resolution provide more than 800 hundred variables equally spaced between 900 and 1750 cm−1, which are highly correlated with each other. Principle component analysis (PCA) was used to calculate principle components and reduce the number of input variables for the following advanced statistical analysis. PCA and significant factor analysis (SFA) suggested that at least 6 PCAs or significant factors are required to characterize original spectroscopic data. All classification methods used in this study were tested with 5, 6, 7 . . . 20 Principle Components (PCs). Preliminary analysis demonstrated that higher classification accuracy can be obtained with statistical methods which are able to model nonlinear relations between variables, such as methods based on support vector machines and artificial neural networks. Multilayer perceptrons (MLP), Radial Basis Function (RBF), and support vector machine (SVM) learning methods were applied for AD diagnostics.

The Neural Network Toolbox (Mathworks, Nattick) was used for modeling, testing, and validation of neural networks. SVM models were designed and implemented using a partial least squares (PLS) toolbox (Eigenvector Research, Inc.) algorithm implemented in a Matlab environment. Optimal MLP architecture was determined by varying the number of hidden layers between one and two and number of neurons in each layer between 10 and 600 for the first hidden layer and 5-50 for the following hidden layers. Additionally, three transfer functions (linear, tangent sigmoidal, and log sigmoidal) and five back-propagating training algorithms (Levenberg-Marquardt, Gradient descent, Powell-Beale conjugate gradient, Bayesian regularization, and Fletcher-Powell conjugate gradient) were tested. Optimal RBF architecture was determined by varying the number of neurons between 10 and 600 and the radius value of the function between 1 and 50. The SVM algorithm was tested with radial basis function and linear kernels.

For each classification model control, mild, and moderate AD data sets were randomly split in to training (70%), testing (15%), and validating (15%) data subsets. Performance of calculated classification models was confirmed using sensitivity (true positive rate) and selectivity (true negative rate) parameters of classification of testing and validating data subsets. Each type of network architecture was tested ten times with new random split of control, mild, and moderate AD data sets for each time. In total, more than 30,000 models were built. Classification models which demonstrated similar performance parameters (sensitivity and selectivity) for testing and validating data subsets were accepted for the following considerations. If the difference in sensitivity (or selectivity) of testing and validating data classifications was more than 10%, the classification model was interpreted as the result of convergence to a local minima with weak generalization properties.

Table 2 presents the best results achieved for selected structures of MLP and RBF networks for Control vs. Moderate AD classification. The third column, entitled "Network structure", contains network descriptors, where the first number is the number of input neurons (the number of PC used), the last number represents the number of output neurons, while the other numbers indicate how many neurons were used in correspondent hidden layers.

TABLE 2

Performance of the selected eight Artificial Neural Network (ANN) architectures in discrimination of Moderate AD from Control spectroscopic data. Maximum and minimum (in parentheses) values of ten independent calculations are shown.

| Model # | Type of network | Network structure | Sensitivity | Selectivity |
|---|---|---|---|---|
| 1 | MLP | 5-20-20-1 | 97 (89) % | 95 (90) % |
| 2 | MLP | 5-50-10-1 | 96 (92) % | 96 (91) % |
| 3 | MLP | 5-100-1 | 96 (93) % | 95 (89) % |
| 4 | MLP | 7-200-20-1 | 96 (92) % | 94 (90) % |
| 6 | RBF | 5-20-20-1 | 95 (90) % | 94 (85) % |
| 7 | RBF | 5-50-10-1 | 96 (91) % | 95 (90) % |
| 8 | RBF | 5-100-1 | 94 (90) % | 94 (89) % |
| 9 | RBF | 7-200-20-1 | 94 (87) % | 94 (91) % |

MLP networks demonstrate slightly better performance in terms of sensitivity and selectivity of classification models (Table 2). Note the variability of these parameters for independent implementations of the selected neuron network. For example, for the 5-20-20-1 MLP network (row #1), sensitivity of correct classification of the AD spectra was observed in the range of 89-97% for ten independent modeling events. These results demonstrated the possibility of building a classification model with high performance parameters. The observed level of instability in classification accuracy can be attributed to two main aspects of the Artificial Neural Network (ANN) modeling process. The first aspect to be considered is intrinsic properties of the experimental data set such as limited size of Raman data set, destructive contribution of noise, and high level of similarity of Raman data. The ideal (100% in sensitivity and specificity) discrimination between groups should not be expected, as only relatively minor changes in biochemical composition of blood serum are likely to be associated with AD progression. Also, intrinsic inhomogeneity of serum samples exposed by the applied drying process does not guarantee that every recorded Raman spectrum will display some evidence of AD. Therefore, achieved level (more than 95% for validating data sets) of accurately classified single Raman spectra is a remarkable result. The second aspect is a propensity of ANN algorithms to fall into local minima yielding reduced generalization ability (Everitt et al., *Applied Multuvariate Data Analysis*, John Wiley & Son, Ltd (2001); Cheng et al., *Statistical Sci.* 9:2-30 (1994), which are hereby incorporated by reference in their entirety). From a practical point of view, ANN models with the highest validated classification accuracy can be accepted. Validation is a crucial step of classification model development as neuron networks frequently can be overtrained. For example, in the course of ANN architectures screening, cases were observed when the accuracy of classification was close to 100% for training data and only ~70% for testing and validating data.

SVM-based algorithms do not tend to be converged on local minima and often outperform alternative classification methods including ANN (Deng et al., *Support Vector Machines: Optimization Based Theory, Algorithms, and*

Figure 2:
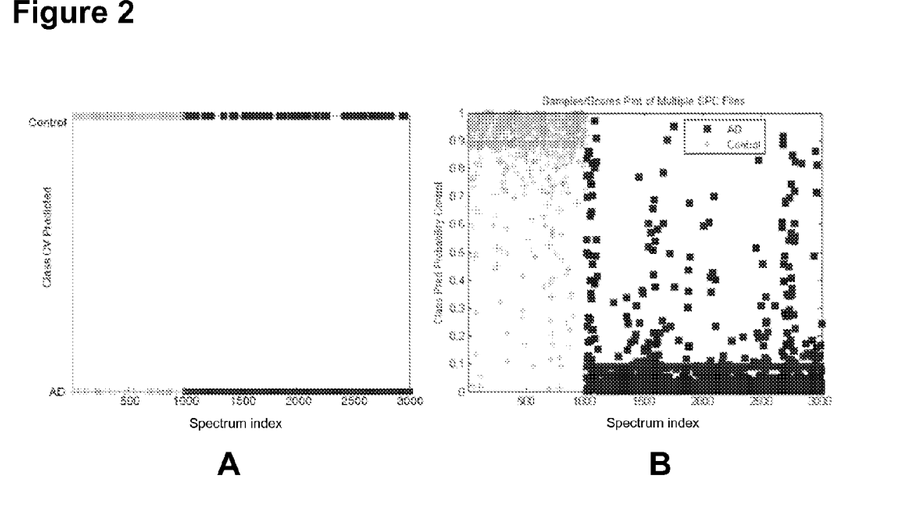
FIG. 2A shows cross-validated classification of Raman spectra, where blue squares represent Raman spectra originated from AD subjects and light blue crosses represent Raman spectra originated from healthy control subjects.
FIG. 2B shows calculated probability for single Raman spectra to be classified as a spectrum acquired from human blood serum of healthy control subjects. Ideal classification would result in all blue squares and light blue crosses placed at AD and Control levels (see Y-axis labels) correspondingly. Blue squares at Control level and light blue crosses at AD level represent misclassified Raman spectra. Table 1 show the performance parameters of the obtained classification model. AD and Control levels in FIG. 2B show the degree of assignment of an individual spectrum to one of these two classes based on the developed statistical model. The X axis represents individual Raman spectra placed consecutively in groups corresponding to individual blood samples.
Figure 3:
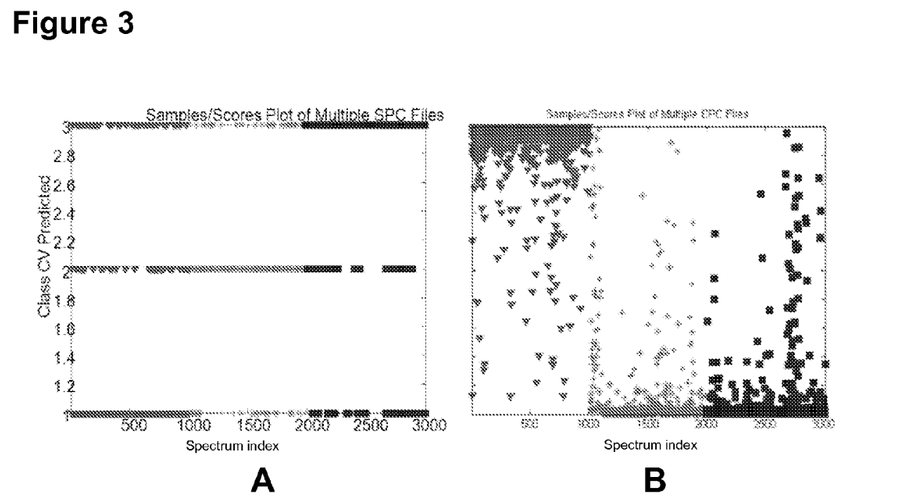
FIG. 3A shows Cross-validated classification. Color code: red triangles—healthy control, green stars—mild AD, blue squares—moderate AD Raman spectra.
FIG. 3B shows calculated probability for single Raman spectra to be classified as a spectrum acquired from human blood serum of healthy control subjects. The X axis represents individual Raman spectra placed consecutively in groups corresponding to individual blood samples.

Extensions, A Chapman & Hall, CRC Press, Taylor & Francis Group, (2013), which is hereby incorporated by reference in its entirety). In the present case, performance parameters of the best calculated SVM classification models were slightly lower than those of ANN models. FIG. 2 and FIG. 3 show results of support vector machines discrimination analysis (SVMDA) classification of Raman spectra for binary (Control vs AD, where AD (mild plus moderate)) and tertiary (control, mild, moderate AD) classification models. These figures show the compilation of several classification models. Every single spectrum was set aside from the training set and then tested by calculated SVM model as a member of a test data set. Usually, less than 10% of spectra from testing data sets were misclassified. The actual result of classification will depend on thresholds values which can be arbitrarily set to the particular values (FIG. 2B and FIG. 3B). The best achieved cross-validated sensitivity and specificity parameters for healthy controls were 93 and 89% (binary classification), respectively (see Table 3, lines 1-2). Similar performance parameters were obtained for a three-class classification model (FIG. 3, Table 3). In this case, moderate and mild AD data were treated as separate classes.

Somewhat greater sensitivity and specificity levels were obtained when just mentioned three classes were treated in pairwise manner. Sensitivity and specificity values of control versus mild AD (lines 6 and 7), control versus moderate AD (lines 8 and 9), and mild versus moderate AD (lines 10 and 11) classification are shown in Table 3. These binary classifiers considered together provide just about 94% in overall quality of AD stage determination.

Table 3 summarizes classification results achieved using SVM, RBF and MLP methods.

All calculations were repeated using donorwise cross-validation. One hundred ANN architectures, which demonstrated the best results in tests where the factor of donors was not considered (Table 3), were tested with data sets formed by eliminating at once all Raman spectra obtained from one of the donors. This classification was repeated 10 times for each donor. Importantly, it was always possible to attain an ANN classification model with more than 60% correctly classified spectra. In other words, using this number as a decision threshold all donors can be correctly diagnosed. Table 3 show minimum and maximum (columns 3, 5, . . . , 13) percentages of correctly classified spectra for donorwise cross-validation. The relatively low numbers as well as their wide range indicate that the power of classification models depends on how donors were split between training and testing data sets. A significant increase in the number of donors will allow addressing the effect of population and physiological factors directly. It is also expected that the increase in the number of donors will eliminate the dependence of the classification model on how donors were split between training and testing data sets.

Example 5—Surface Enhanced Raman Spectroscopy (SERS) of Blood for AD Diagnostics Surface enhanced Raman spectroscopy (SERS) of human serum combined with advanced statistical analysis was used to develop a simple blood test for Alzheimer's disease detection. High quality SERS spectra were collected after mixing human serum samples directly with the colloidal silver nanoparticles. SERS spectra were measured for the three groups of blood serum samples. The first group includes patients with clinically confirmed Alzheimer's disease (AD). Two other groups include non-AD control subjects. These two non-AD groups of subjects were from elderly volunteers (Healthy Control subjects) and from subjects with other types of dementia (Other than AD). A statistical algorithm was constructed based on support vector

| | | SVM | | | RBF | | | MLP | | | |
|---|---|---|---|---|---|---|---|---|---|---|---|
| | | CV sensitivity/% | | CV specificity/% | | CV sensitivity/% | | CV specificity/% | | CV sensitivity/% | | CV specificity/% | |
| # | Class 1 | Spect 2 | Donor 3 | Spect 4 | Donor 5 | Spect 6 | Donor 7 | Spect 8 | Donor 9 | Spect 10 | Donor 11 | Spect 12 | Donor 13 |
| | | | | | Two classes model | | | | | | | |
| 1 | Healthy Controls | 93(88) | 75-84 | 90(75) | 69-85 | 95 | 72-88 | 92 | 65-87 | 97 | 68-87 | 96 | 65-90 |
| 2 | AD | 90(75) | 69-85 | 93(88) | 75-84 | 92 | 65-87 | 95 | 72-88 | 96 | 65-90 | 97 | 68-87 |
| | | | | | Three classes model | | | | | | | |
| 3 | Healthy Controls | 88(76) | 62-78 | 92(81) | 64-77 | 89 | 67-77 | 92 | 68-83 | 92 | 68-89 | 93 | 67-88 |
| 4 | Mild | 83(73) | 64-80 | 95(80) | 63-81 | 85 | 66-84 | 94 | 70-85 | 92 | 67-84 | 95 | 67-85 |
| 5 | Moderate | 87(78) | 72-83 | 92(83) | 64-81 | 86 | 73-80 | 93 | 71-86 | 93 | 68-85 | 94 | 68-85 |
| | | | | | Healthy Controls vs Mild AD model | | | | | | | |
| 6 | Healthy Controls | 94(89) | 73-90 | 90(84) | 68-91 | 96(89) | 61-90 | 89 | 67-87 | 95 | 59-92 | 91 | 64-91 |
| 7 | Mild | 90(84) | 68-91 | 94(89) | 73-90 | 89(84) | 67-87 | 96 | 61-90 | 91 | 64-91 | 95 | 59-92 |
| | | | | | Healthy Controls vs Moderate AD model | | | | | | | |
| 8 | Healthy Controls | 94(85) | 75-89 | 93(84) | 72-84 | 94(85) | 71-86 | 94 | 70-85 | 94 | 68-85 | 94 | 67-88 |
| 9 | Moderate AD | 93(84) | 72-84 | 94(85) | 75-89 | 94(84) | 70-85 | 94 | 71-86 | 94 | 67-88 | 94 | 68-85 |
| | | | | | Mild AD vs Moderate AD model | | | | | | | |
| 10 | Mild AD | 91 | 70-85 | 93 | 72-86 | 93 | 69-87 | 93 | 70-84 | 93 | 68-87 | 94 | 60-87 |
| 11 | Moderate AD | 93 | 72-86 | 91 | 70-85 | 93 | 70-84 | 93 | 69-87 | 94 | 60-87 | 93 | 68-87 | machine (SVM) classifier to facilitate the detection of minor changes in blood serum composition caused by AD. A Minimum Redundancy Maximum Relevance (MRMR) feature selection algorithm was used to select the best subset of features to be used for the differentiation between control and AD samples. SVM-based Discriminant analysis of SERS spectra of blood serum allowed for differentiating AD patients and control subjects with very high sensitivity and specificity. This pilot study provides strong basis for the application of SERS-based human serum analysis for the development of a simple blood test for AD detection.

Silver colloid nanoparticles were prepared using a previously reported protocol (Leopold et al., *The Journal of Physical Chem. B* 107:5723-5727 (2003), which is hereby incorporated by reference in its entirety). Nanoparticles prepared by this method have been successfully used for the detection of different types of cancer and separation from healthy control group by SERS (Feng et al., *Biosens Bioelectron* 25:2414-2419 (2010); Feng et al., *Biosensors and Bioelectronics* 26:3167-3174 (2011), which are hereby incorporated by reference in their entirety).

Prior to Raman measurements, a serum sample was defrosted on ice and a 40-μL drop was mixed with silver colloid nanoparticles in 1:1 ratio. Then, a 40-μL drop of the mixture was placed on a microscope glass slide covered with aluminum foil and allowed to dry completely under gentle air flow within 15 minutes. This resulted in the formation of a thin cast film. The aluminum foil was used as a deposition surface to reduce a fluorescence background.

The Raman spectra of serum samples were measured using a Renishaw in Via confocal Raman spectrometer equipped with a research-grade Leica microscope, 20× long-range objective. 10 Raman spectra with one 10-s accumulation for each sample were collected from different spots. A 785-nm laser light was utilized for excitation. The laser power on the sample was approximately 11.5 mW (10% laser power), which is low enough to avoid sample photodamage. The spot size of the excitation beam on the sample was 5 μm (standard confocal mode) and the spectral resolution was about 1 cm$^{-1}$. A silicon standard was used for instrument calibration.

All SERS spectra were uploaded into MatLab software package and treated the same way as discussed for Normal Raman experiments.

Example 6—Data Treatment

Figure 4:
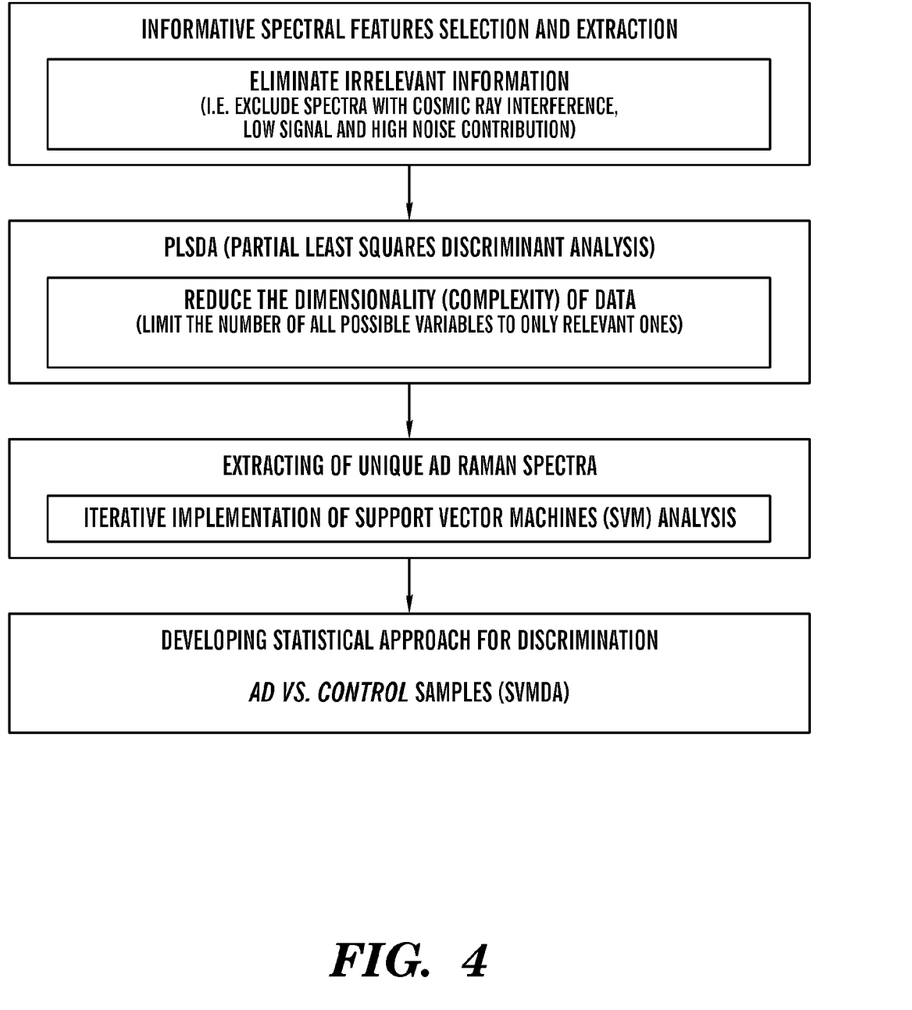
FIG. 4 shows a schematic representation of four major steps in the classification approach of the present invention.

The spectra were imported into MATLAB 7.9.0 for statistical analysis. All spectra with cosmic ray interference were excluded as well as non-informative spectra consisted of noise primary. The number of principal components in the basis set were determined using significant factor analysis (SFA), and the individual component spectra were extracted using the partial least squares (PLS) function. The Curve Fitting Toolbox in MATLAB was used to perform residual analysis on the difference between the fitted and experimental spectra, and "goodness-of-fit" statistics were calculated based on how well the signature matches the experimental spectrum. Unique AD Raman spectra were then extracted by iterative implementation of the support vector machines (SVM) analysis. These spectra were used for constructing the discrimination between different diagnostic categories. SVM-based methodology was chosen, because it was successfully implemented in development of diagnostic classification of serum for another disease (Martin et al., *Analyst*, 129:897 (2004), which is hereby incorporated by reference in its entirety). FIG. 4 shows a schematic representation of four major steps in our classification approach.

Figure 5:
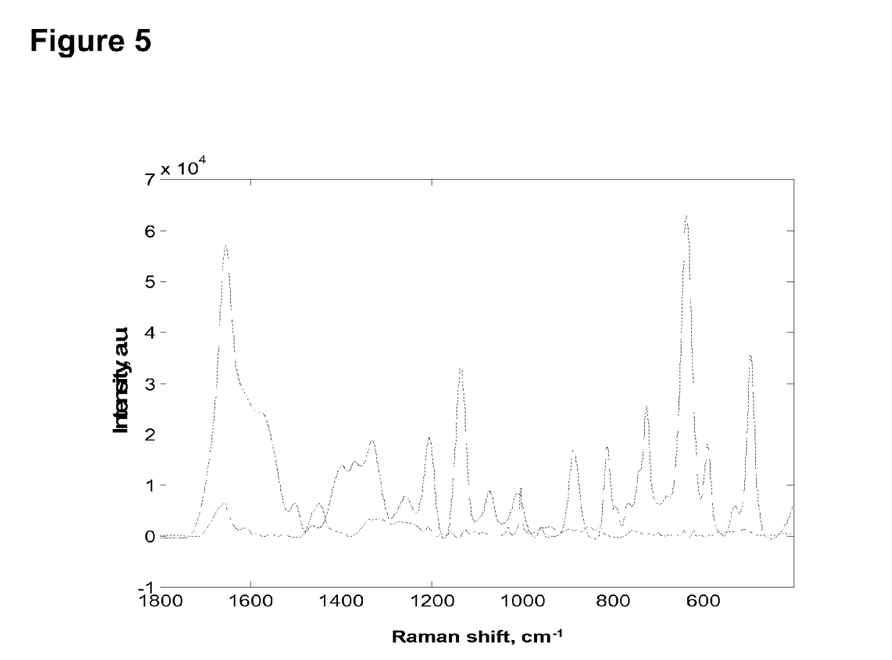
FIG. 5 shows SERS and Raman spectra of serum samples. Mean SERS spectra of human blood serum are shown in red and mean Raman spectra of human blood serum is shown in green.

FIG. 5 illustrates the power of SERS in terms of signal enhancement. However, it should not be concluded that Normal Raman technique yields poor results in comparison to SERS results. The power of SERS can be used in combination with Normal Raman Spectroscopy as a complimentary technique to resolve difficult diagnostic cases. For example, the combination of SERS and Normal Raman data could be used to conduct differential diagnostic tests for symptomatically similar dementias, which nevertheless have different underlying pathology and have to be treated specifically.

TABLE 4

Summary of the statistical results for the models illustrated below.
The confidence interval for all models was set at 95%.

| SVMDA model | # of AD subjects | # of control subjects | Sensitivity (Cal): | Specificity (Cal): | Sensitivity (CV): | Specificity (CV): | Class. Err (CV): | Class. Err (CV): | RMSE (CV): |
|---|---|---|---|---|---|---|---|---|---|
| AD vs HC | 10 | 10 | 0.990 | 0.980 | 0.900 | 0.890 | 0.015 | 0.105 | 0.045 |
| AD vs OD | 10 | 6 | 1.000 | 1.000 | 0.989 | 1.000 | 0.001 | 0.005 | 0.001 |
| MAD vs mAD vs HC | 20 (10 Moderate and 10 Mild stage) | 10 | 1.000 | 0.955 | 0.820 | 0.880 | 0.022 | 0.150 | 0.223 |

*Abbreviations: SVMDA—support vector machines discrimination analysis, AD—Alzheimer's disease, OD—other types of dementia control subjects, MAD—moderate stage AD, mAD—mild stage AD, HC—elderly healthy control subjects, Cal—calibration, CV—cross-validation, Class—classification, Err—error, RMSE—root mean square error.

Figure 6:
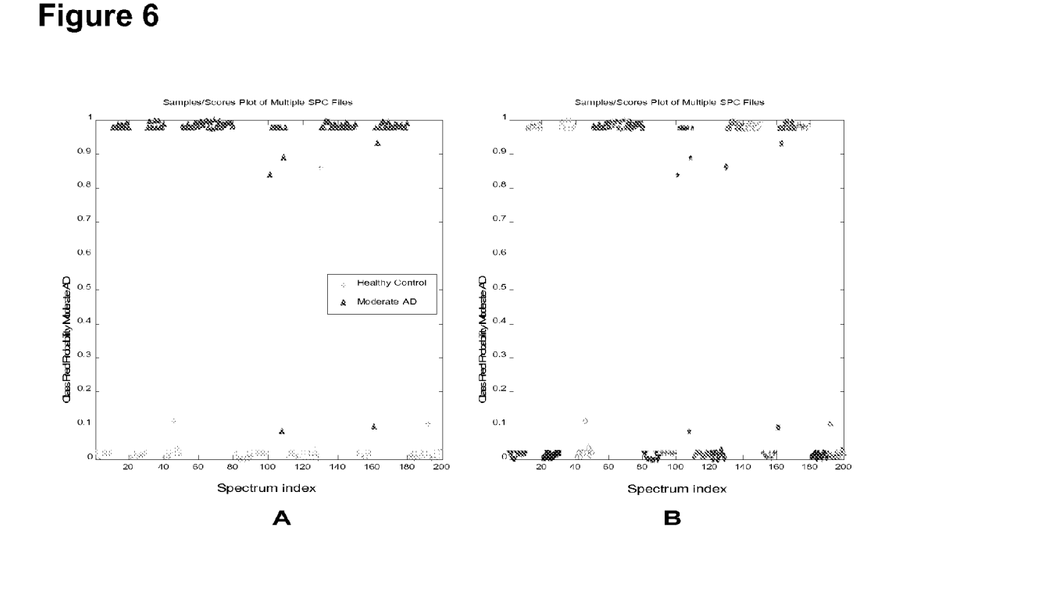
FIG. 6A shows probability of the training dataset to be identified as AD class (quality of the model). Moderate AD samples were used to build the model.
FIG. 6B shows representation of the same model using subject-colored settings in order to illustrate that the majority of spectra obtained for an individual blood sample were classified correctly.

SVM Discriminant analysis of SERS spectra of serum allowed for the differentiation between AD patients and healthy individuals (FIGS. 6A-B). Red triangles and blue squares correspond to a single spectra acquired from AD and control samples, respectively. FIG. 6A shows the probability of the training dataset to be identified as AD class (quality of the model). FIG. 6B shows a representation of the same model using subject-colored settings. Each AD serum sample was classified correctly in the majority of the spectra; however only one spectrum out of 10 from just one healthy subject had a high AD probability score.

Figure 7:
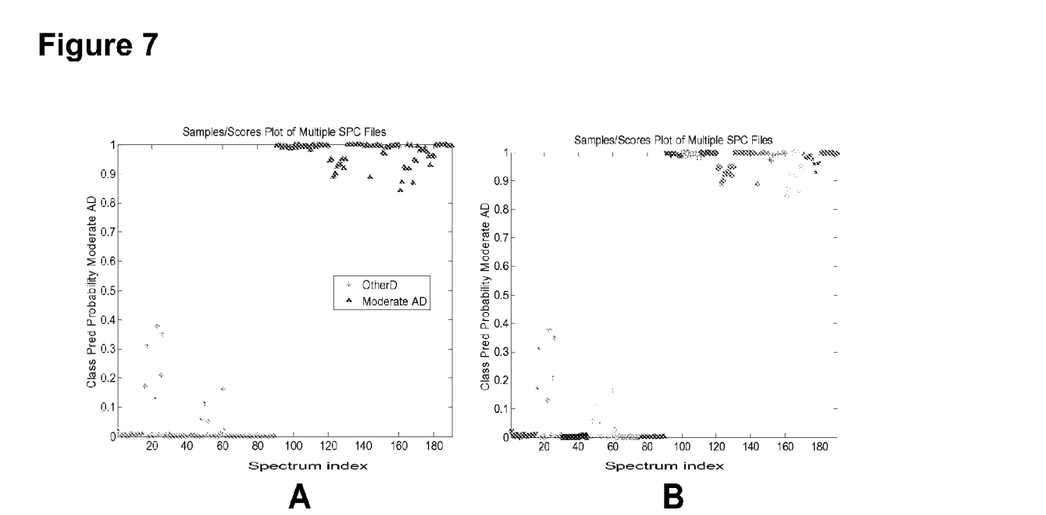
FIG. 7A shows probability of the training dataset to be identified as AD class (quality of the model).
FIG. 7B shows representation of the same model using subject-colored settings.

SVM Discriminant analysis of SERS spectra of serum allowed for the differentiation between AD patients and individuals with other types of dementia (FIGS. 7A-B). Red triangles and green squares correspond to a single spectra acquired from AD and other types of dementia samples, respectively. FIG. 7A shows the probability of the training dataset to be identified as AD class (quality of the model). FIG. 7B shows representation of the same model using subject-colored settings. Each AD serum sample was classified correctly in the majority of the spectra, while no spectra were classified as AD for individuals with other types of dementia. The effects of the drugs do not cause classification errors since all of the subjects were on their medication regimen.

Figure 8:
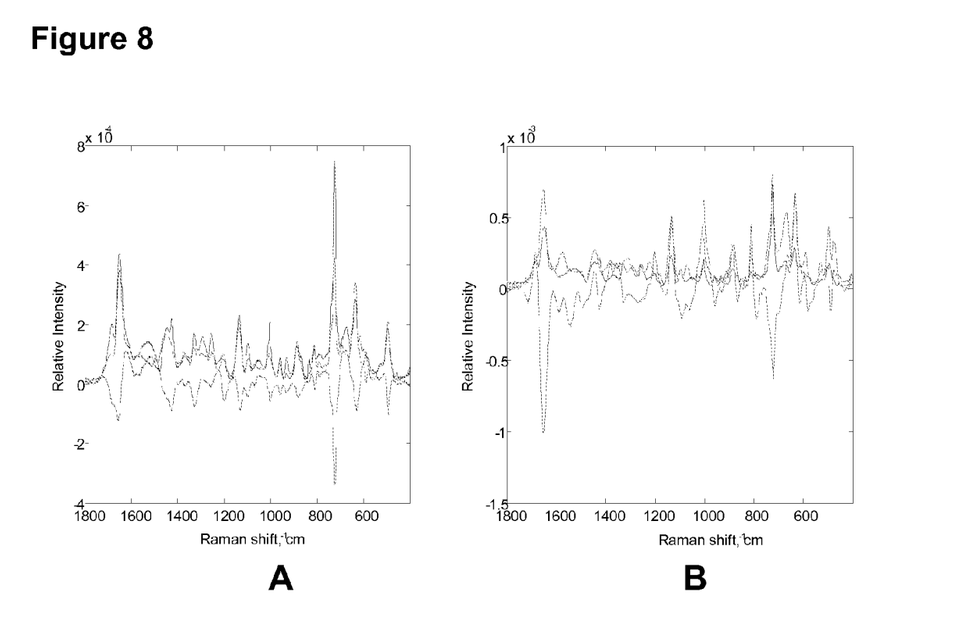
FIG. 8A shows a mean AD spectrum subtracted from mean healthy controls spectrum.
FIG. 8B shows a mean AD spectrum subtracted from other dementia controls spectrum.

Standard deviations for each class of SERS spectra of serum samples are shown on FIGS. 8A-B, with the standard deviation for AD class of spectra being a blue line and for control samples being a green line. The difference spectrum is shown as a red line: a mean AD spectrum subtracted from mean healthy controls spectrum on the left and mean AD spectrum subtracted from other dementia controls spectrum on the right. This picture is shown to illustrate the definite presence of some difference between sample classes under the study. The SVM Discriminant analysis was not based on these differences since the algorithm itself calculates virtual variables which are characteristic to each class.

Figure 9:
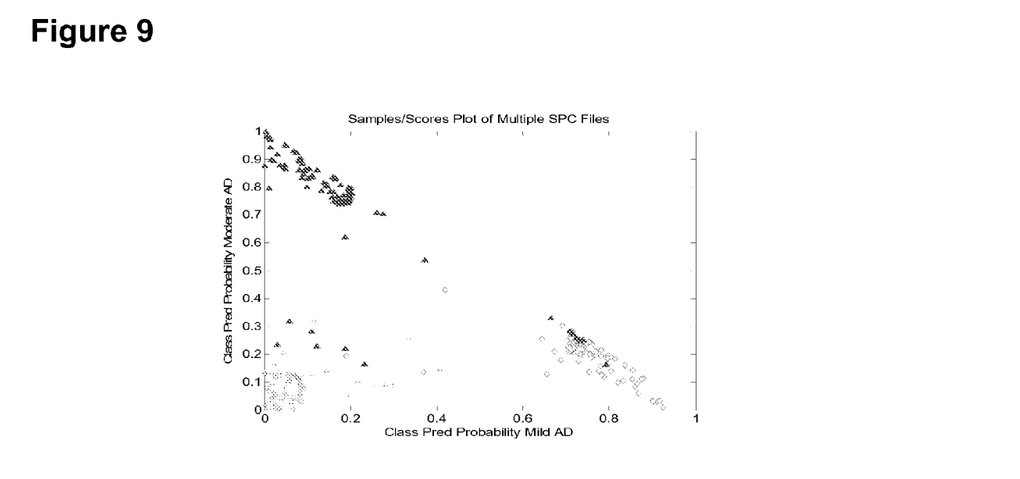
FIG. 9 shows that SVM Discriminant analysis of SERS spectra of serum allows for the differentiation between AD patients and healthy individuals. Red triangles, white diamonds, and blue crosses correspond to single spectra acquired from moderate AD, mild AD and control samples, respectively. The picture shows the probability of each spectrum to be assigned to either Moderate AD class (on the y-axis) or to the Mild AD class (on the x-axis) or to be identified as healthy elderly control class (quality of the model).

SVM Discriminant analysis of SERS spectra of serum allowed for the differentiation between AD patients and healthy individuals (FIG. 9). Red triangles, white diamonds, and blue crosses correspond to a single spectra acquired from moderate AD, mild AD, and control samples, respectively. The picture shows the probability of each spectrum to be assigned to either Moderate AD class (on the y-axis) or to the Mild AD class (on the x-axis) or to be identified as healthy elderly control class (quality of the model). Each AD serum sample showed several spectra classified as AD, both for mild and moderate AD. No spectra were classified as AD for healthy individuals.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method for detecting Alzheimer's disease in a human subject, said method comprising:
providing a sample from the human subject, wherein the sample is whole blood, plasma, cerebral spinal fluid, or human serum;
subjecting different regions of the sample individually to a Raman spectroscopic analysis to produce a separate Raman spectrum for each of the different regions of the sample, wherein said sample contains biomolecules whose structural, conformational, and compositional variations contribute to differences in the Raman spectra of the sample and wherein said subjecting different regions of the sample individually to a Raman spectroscopic analysis is carried out according to a pre-programmed mapping procedure which detects said variations;
subjecting the Raman spectra collected from the different regions of the sample to a statistical analysis;
generating a representation of each separate Raman spectrum based on the statistical analysis;
preparing Raman spectroscopic signatures for the sample based on the representation for each separate Raman spectrum;
determining whether each of the Raman spectroscopic signatures for the sample corresponds to an Alzheimer's disease spectroscopic signature; and
identifying a subject as having Alzheimer's disease where the Raman spectroscopic signature for the sample from that subject corresponds to the Raman spectroscopic signature for Alzheimer's disease.

2. The method of claim 1 further comprising:
determining the stage of Alzheimer's disease in the subject based on the Raman spectroscopic signature for the sample from the subject.

3. The method of claim 2, wherein said method determines the stage of Alzheimer's disease as being mild or moderate.

4. The method of claim 1, wherein said determining comprises:
comparing the Raman spectroscopic signature for the sample from the subject to a reference Raman spectroscopic signature and
determining the presence of Alzheimer's disease in the subject based on said comparing.

5. The method of claim 4 further comprising:
determining the stage of Alzheimer's disease in the subject based on the Raman spectroscopic signature for the sample from the subject.

6. The method of claim 5, wherein said method determines the stage of Alzheimer's disease as being mild or moderate.

7. The method of claim 1 further comprising:
determining whether the subject has a neurodegenerative disease other than Alzheimer's disease based on the Raman spectroscopic signature for the sample from the subject.

8. The method of claim 1, wherein the Raman spectroscopic analysis is selected from the group consisting of NIR Raman spectroscopy and Surface Enhanced Raman spectroscopy (SERS).

9. The method of claim 1, wherein statistical analysis is selected from the group consisting of Principle component analysis (PCA), Partial Least Squares Discriminant Analysis (PLSDA), Multilayer perceptrons (MLP), Radial Basis Function (RBF), artificial neural network (ANN), support vector machine (SVM), and SVM-based Discriminant analysis.

10. The method of claim 1, wherein said subjecting different regions of the sample individually to Raman spectroscopic analysis is carried out by iteratively implementing the statistical analysis to said representation of each separate Raman spectrum to create the Raman spectroscopic signature for the sample.

11. A method for monitoring Alzheimer's disease progression in a human subject, said method comprising:
providing a sample from a human subject with Alzheimer's disease, wherein the sample is whole blood, plasma, cerebral spinal fluid, or human serum;
subjecting different regions of the sample individually to a Raman spectroscopic analysis to produce a separate Raman spectrum for each of the different regions of the sample, wherein said sample contains biomolecules whose structural, conformational, and compositional variations contribute to differences in the Raman spectra of the sample and wherein said subjecting different regions of the sample individually to a Raman spectroscopic analysis is carried out according to a pre-programmed mapping procedure which detects said variations;
subjecting the Raman spectra collected from the different regions of the sample to a statistical analysis;
generating a representation of each separate Raman spectrum based on the statistical analysis;

preparing Raman spectroscopic signatures for the sample based on the representation for each separate Raman spectrum;

comparing each of the Raman spectroscopic signatures for the sample to a prior Raman spectroscopic signature from the subject or to a Raman spectroscopic signature standard for a specific stage of Alzheimer's disease; and determining the progression of Alzheimer's disease in the subject based on said comparing.

12. The method of claim 11, wherein the Raman spectroscopic signature for the sample is compared to a prior Raman spectroscopic signature from the subject during said comparing.

13. The method of claim 11, wherein the Raman spectroscopic signature for the sample is compared to a Raman spectroscopic signature standard for a specific stage of Alzheimer's disease.

14. The method of claim 13, wherein the Raman spectroscopic signature standard is for mild stage Alzheimer's disease.

15. The method of claim 13, wherein the Raman spectroscopic signature standard is for moderate stage Alzheimer's disease.

16. The method of claim 11, wherein the Raman spectroscopic analysis is selected from the group consisting of NIR Raman spectroscopy and Surface Enhanced Raman spectroscopy (SERS).

17. The method of claim 11, wherein statistical analysis is selected from the group consisting of Principle component analysis (PCA), Partial Least Squares Discriminant Analysis (PLSDA), Multilayer perceptrons (MLP), Radial Basis Function (RBF), artificial neural network (ANN), support vector machine (SVM), and SVM-based Discriminant analysis.

18. The method of claim 11, wherein said subjecting different regions of the sample individually to Raman spectroscopic analysis is carried out by iteratively implementing the statistical analysis to said representation of each separate Raman spectrum to create the Raman spectroscopic signature for the sample.

* * * * *